(12) United States Patent
Schlottig et al.

(10) Patent No.: US 8,734,889 B2
(45) Date of Patent: May 27, 2014

(54) DENTAL IMPLANT AND METHOD FOR THE PRODUCTION THEREOF

(75) Inventors: Falko Schlottig, Fullinsdorf (CH); Thomas Hefti, Basel (CH)

(73) Assignee: Thommen Medical AG, Waldenburg (CH)

( * ) Notice: Subject to any disclaimer, the term of this patent is extended or adjusted under 35 U.S.C. 154(b) by 1310 days.

(21) Appl. No.: 11/916,749

(22) PCT Filed: Jun. 1, 2006

(86) PCT No.: PCT/CH2006/000296
§ 371 (c)(1),
(2), (4) Date: Dec. 6, 2007

(87) PCT Pub. No.: WO2006/131010
PCT Pub. Date: Dec. 14, 2006

(65) Prior Publication Data
US 2008/0213726 A1 Sep. 4, 2008

(30) Foreign Application Priority Data

Jun. 6, 2005 (CH) ..................................... 0947/05

(51) Int. Cl.
*A61L 33/00* (2006.01)
(52) U.S. Cl.
USPC ............ 427/2.1; 205/229; 205/640; 205/363; 205/364; 205/717; 427/2.24; 427/2.25; 427/2.26; 427/331; 427/343; 623/23.5; 623/23.56; 623/23.51; 134/2; 433/173; 433/174; 424/423
(58) Field of Classification Search
USPC ...................... 623/23.51, 16, 66, 23.5, 23.56; 433/173; 424/423; 205/640, 229, 322, 205/675, 705, 717; 427/2.1, 2.24, 2.25, 427/2.26, 331, 343
See application file for complete search history.

(56) References Cited

U.S. PATENT DOCUMENTS 5,071,351 A * 12/1991 Green et al. .................. 433/173
6,025,536 A * 2/2000 Bender et al. ............... 623/23.53
(Continued)

FOREIGN PATENT DOCUMENTS

DE 2641695 A1 3/1978
DE 129195 * 4/1978 ............. B28B 11/08
(Continued)

OTHER PUBLICATIONS

Hirao et al., Microstructure Control of Silicon Nitride by Seeding with Rolike [Beta]-Silicon Nitride Particles, 1994, Journal of American Ceramics Society, vol. 77, Ed. 7, pp. 1857-1862.*

(Continued)

*Primary Examiner* — Dah-Wei D Yuan
*Assistant Examiner* — Andrew Bowman
(74) *Attorney, Agent, or Firm* — Sughrue Mion, PLLC

(57) ABSTRACT

The invention relates to a ceramic implant, especially a dental implant, comprising a structured or porous surface for at least partially inserting into a bone. An especially advantageous surface is obtained when it is at least partially modified by a salt melt. These excellent osteointegration properties can be obtained by a method whereby the surface is modified in a salt melt at least in the regions exposed to the bones and/or soft tissue, optionally following a previous modification of the surface whereby material has been removed.

21 Claims, 5 Drawing Sheets

(56) References Cited

U.S. PATENT DOCUMENTS

| | | | |
|---|---|---|---|
| 6,527,938 B2 * | 3/2003 | Bales et al. | 205/229 |
| 6,712,952 B1 * | 3/2004 | Fray et al. | 205/640 |
| 2002/0072807 A1 * | 6/2002 | Nawa et al. | 623/23.51 |
| 2004/0267376 A1 * | 12/2004 | Suzuki et al. | 623/23.5 |

FOREIGN PATENT DOCUMENTS

| | | | |
|---|---|---|---|
| DE | 3015529 A1 | 11/1980 | |
| DE | 4114792 A1 | 11/1992 | |
| DE | 19530981 A1 | 2/1997 | |
| DE | 19944970 C1 | 4/2001 | |
| EP | 0388576 A1 | 9/1989 | |
| FR | 2721196 A1 | 12/1995 | |
| JP | 61-201642 A | 9/1986 | |
| WO | 01/32228 A1 | 5/2001 | |

OTHER PUBLICATIONS

Roche Lexikon Medizin, 5. Auflage, Urban & Fischer, Munchen-Jena 2003 (1984, 1987, 1993, 1999, 2003) pp. 1-5.

Daniel Buser 25 Titanium for Dental Applications (II): Implants With Roughened Surfaces University of Berne, School of Dental Medicien, Department of Oral Surgery and Stomatology, Berne, Switzerland, pp. 876-888.

24 Dental Applications (I) pp. 834-836.

D.M. Brunette, P. Tengvall, M. Textor and P. Thomsen, Titanium in Medicine, Springer, http://www.titaniuminmedicine.com.

Marion L. Maroney, A Guide to Metal and Plastic Finishing. Abrasives, Chapter 6, Types of Abrasives, pp. 23-27.

Fukushima, et al. (1979), Nucleatin and Growth, Table 2.1 Heat of Adsorption ($AH$) of Hydrogen on Metals, pp. 60-92.

Techniques: Practical Aspects, Chapter 4, pp. 114-123.

Allen M. Hermann, series editor. Applied Physics, University of Colorado at Boulder, R.K. Pandey, et al., Handbook of Semiconductor Electrodeposition, Marcel Dekker, Inc.

George J. Rudzki, Surface Finishing Systems, Metal and Non-Metal Finishing Handbook-Guide.

M.J. O'Keefe, et al., The Science, Technology and Materials Applications of Physical Vapor Deposition Processes, pp. 151-183.

* cited by examiner

DENTAL IMPLANT AND METHOD FOR THE PRODUCTION THEREOF

TECHNICAL FIELD

The present invention relates to an implant, especially a dental implant, with a porous surface for at least partial insertion into a bone and with improved osteointegration properties. The implant here is ceramic, but it can also be metallic. The present invention further relates to a method for the production of such an implant and to uses of such an implant.

PRIOR ART

Injured or damaged parts of the hard tissue and/or soft tissue of the human body are best restored by using endogenous hard tissue and/or soft tissue. For various reasons, this is not always possible, and synthetic material is therefore used in many cases as a temporary replacement material (being biodegradable or being removed postoperatively) or as a permanent replacement material.

Implants anchored in the hard tissue and/or soft tissue are used for the temporary or permanent replacement or support of parts of the locomotor apparatus that have been damaged as a result of accident, wear, deficiency or disease or have otherwise degenerated, including in particular parts of the masticatory apparatus. Implant normally designates an artificial and chemically stable material that is introduced into the body as a synthetic replacement or for mechanical strengthening (see, for example, Roche Lexikon Medizin, published by Urban & Fischer; 5th edition, 2003). The support or replacement function in the body is afforded on the basis of the mechanical properties and implant design. Thus, for example, hip-joint and knee-joint prostheses, spinal column implants and dental implants have for many years been successfully used in clinical practice.

In terms of the anchoring of the implant and the compatibility of the implant at the interface between implant surface and adjoining tissue, great importance is attached to the implant surface. Thus, measurements have shown that implants with a smooth surface are anchored only to a minimal extent in the bone (poor osteointegration), almost irrespective of the base material used, whereas implants with a structured surface permit a good mechanical connection and, with suitable configuration of the surface, also a good biological connection to the surrounding hard tissue or soft tissue (see, for example, Titanium in Medicine, Material Science, Surface Science, Engineering, Biological Responses and Medical Applications Series: Engineering Materials, Brunette, D. M.; Tengvall, P.; Textor, M.; Thomsen, P. (editors)).

The time required for satisfactory incorporation, which is an important and central property of implants, is referred to as the osteointegration time or, in the dental field, also as the osseointegration time. This designates the time that passes until the bone substance has connected sufficiently strongly and permanently with the implant surface, that is to say has as it were become integrated therein.

A wide variety of methods are used for surface treatment and surface structuring [see, for example, A Guide to Metal and Plastic Finishing (Maroney, Marion L.; 1991); Handbook of Semiconductor Electrodeposition (Applied Physics, 5) (Pandey, R. K. et al.; 1996); Surface Finishing Systems: Metal and Non-Metal Finishing Handbook Guide (Rudzki, George J.; 1984); Titanium in Medicine, Material Science, Surface Science, Engineering, Biological Responses and Medical Applications Series: Engineering Materials, (Brunette, D. M.; Tengvall, P.; Textor, M.; Thomsen, P. (editors)) and Materials and Processes for Surface and Interface Engineering (NATO Asi Series; Series E, Applied Sciences, 115, Pauleau, Ives (editor); 1995); and the references cited therein].

Implants are nowadays made from a wide variety of materials, for example titanium, niobium, zirconium, tantalum, of alloys, for example titanium alloys, implant-grade steel, CoCr alloys, various polymers and ceramics, for example based on zirconium oxides, aluminum oxides, titanium oxides, etc.

For many implants, especially tooth implants, titanium and its alloys are mainly used, since these materials have a sufficiently low modulus of elasticity and a relatively high strength. However, measurements have shown that titanium implants with a smooth surface structure only anchor inadequately in bone, whereas implants with a roughened surface provide an appreciably better union between bone and implant in terms of tensile strength and torsional strength.

EP 0 388 576 A1 therefore proposes creating a macro-roughness on a metallic implant surface in a first stage by means of sandblasting, and then superimposing this with a micro-roughness by means of treatment in an acid bath. The implant surface can thus be roughened by means of sandblasting and then treated with an etching agent, for example hydrofluoric acid or a mixture of hydrochloric acid and sulfuric acid. This structuring of the surface creates a secure connection between hard tissue and metal.

In the field of dental implants, titanium, for esthetic reasons, is unsuitable especially in the visible front area of the mouth, because the material looks visibly different than the surrounding hard and soft tissue. It is therefore desirable to use another material, one that does not have these disadvantages. With ceramic materials, for example zirconium oxide, titanium oxide or aluminum oxide, or mixtures thereof, materials are available that have an extremely high degree of strength, particularly when the shaped articles undergo hot isostatic pressing or hot isostatic sealing. A specific yttrium-stabilized zirconium oxide ceramic, for example with 92.1-93.5% by weight of $ZrO_2$, 4.5-5.5% by weight of $Y_2O_3$ and 3.8-2.2% by weight of $HfO_2$, is known from U.S. Pat. No. 6,165,925, for example. Other common ceramics are discussed in the introductory part of said U.S. Pat. No. 6,165,925.

The use of ceramic, for example a zirconium oxide ceramic, a titanium oxide ceramic or an aluminum oxide ceramic, as a material for production of an implant anchored in hard tissue or soft tissue is complicated, since, in order to ensure a sufficient mechanical stability of the ceramic, it is necessary for it to be produced without measurable porosity, this generally resulting at the same time in a smooth and extremely hard surface.

With smooth ceramic surfaces, a direct and sufficiently mechanically stable union with the surrounding hard tissue cannot be anticipated. Therefore, implants made of pure ceramics, such as zirconium oxide, titanium oxide or aluminum oxide or mixtures thereof, have hitherto hardly been used in direct contact with hard tissue. For anchoring in hard tissue, structural composites with metallic implant materials are used, for example in hip endoprosthetics or in oral implantology.

For example, DE 195 30 981 A1 describes a prefabricated and fully ceramic implant construction of zirconium dioxide for obtaining artificial crown stumps supported on implants and with a tooth coloration. The actual implant is made of surface-structured metallic titanium, while the esthetics of the visible part are afforded by a zirconium oxide ceramic.

WO 2004/096075 A1 describes a tooth implant formed by a one-piece main body composed of zirconium oxide or of a zirconium oxide/aluminum mixture. No surface treatment is described, and it is doubtful whether such an implant structure provides sufficient osseointegration at all.

FR 2 721 196 A1 describes a one-piece implant based on zirconium oxide. To improve the osteointegration, the corresponding implant part is intended to be provided with a coating, for example of hydroxyapatite.

WO 03/045268 A1 describes a ceramic implant based on zirconium oxide. The outer face of the anchoring part is at least partially roughened or microstructured by removal of material or is provided with a coating. After blasting treatment, for example by sandblasting, chemical processes are also considered, in particular etching processes, which can be used if appropriate as a secondary treatment to previous mechanical treatment. Initial blasting treatment is preferred in particular, for example by sandblasting with $Al_2O_3$, followed by an etching treatment with phosphoric acid, sulfuric acid, hydrochloric acid or mixtures thereof. The treated implant can also be stored in a suitable liquid, for example deionized water, or in a NaCl solution. In this way, before the dental implant is used, it is possible to avoid the surface losing some or all of its activation as a result of constituents of the air. This therefore promotes osteointegration.

The problem is that, with this kind of combined treatment, the surface roughness remains slight, because of the considerable hardness of the zirconium oxide ceramic, and the ceramic is chemically extremely stable with respect to the treatment with phosphoric acid, sulfuric acid, hydrochloric acid or mixtures thereof.

DISCLOSURE OF THE INVENTION

The object of the invention is therefore to avoid the disadvantages of the prior art and to propose implants which anchor firmly and permanently in the hard tissue and soft tissue and thus show good osteointegration or osseointegration. The specific aim is therefore to propose an improved implant with a structured surface, in particular a porous surface, for at least partial insertion into hard tissue, for example into a bone, and/or into soft tissue, said implant being ceramic. A further aim is to make available a production method suitable for this purpose.

This object is achieved by virtue of the fact that the structured or porous surface is modified at least in some regions in a salt melt or is the result of a salt melt modification. The term "salt melt" is including treatments involving molten salt or fused salt, these terms being used in the field essentially equivalently.

According to the invention, this object is therefore achieved by the implant surface being specifically treated and thereby having specific properties. The treatment can be carried out not only in partial regions of the implant surface but also over the entire surface of the implant.

In the context of this invention, the implants in question are in the first instance implants based on ceramic materials. It is equally possible to structure the surface of metal-based implants with the aid of a salt melt. This aspect is to be regarded to some extent as a separate aspect which in itself has also not been described previously in the prior art and is of an inventive character. Accordingly, it is also possible to provide a metallic implant having a structured or porous surface which is modified at least in some regions in a salt melt or is the result of a salt melt modification. All of the embodiments described below can accordingly be realized equally well on metals, for example in implants based on titanium, zinc, niobium, tantalum, implant-grade steel (or stainless steel) or suitable alloys.

The core of the invention is therefore the surprising finding that implants based on ceramic in particular, but also metal-based implants, can be surface-modified by a salt melt in such a way that they then exhibit excellent osteointegration or osseointegration. It has been found that the osteointegration/osseointegration of a surface thus treated is better than the corresponding values for acid-modified surfaces and/or for surfaces, particularly of ceramics, which have only been provided with a macro-roughness by sandblasting.

The implant is therefore structured on its surface by etching in a salt melt, the etching in the salt melt particularly involving essentially only a removal of material. In other words, the salt melt is not used in order simply to introduce anions or cations, for example, from the salt melt into the surface or, as it were, to create a coating. Instead, the salt melt is in fact used to perform a process of material removal which changes the topography of the surface, in order to obtain a very specifically structured surface.

In fact, it is also found that the surfaces produced according to the invention comprise essentially no constituents introduced from the salt melt used. Thus, the salt melt has essentially only the effect of removing material.

Under suitably adopted conditions, and with a suitable choice of the material of the implant, the resulting topological structure corresponds to a micro-roughness, that is to say preferably a roughness with an order of magnitude of the structure elements in the upper nanometer range or lower micrometer range (e.g. 100 nm-5 μm, preferably 500 nm-2 μm, see also the figures), which can be superposed on an above-mentioned macro-roughness (typically >10-20 μm) effected by mechanical treatment. The surface structure preferably involves a micro-roughness of this kind with a cauliflower-like and/or granular surface topology.

The structuring of the surface preferably takes place entirely without any additional treatment with concentrated acids or bases or aqueous solutions, and instead only by the influence of the salt melt, if appropriate in combination with a mechanical treatment for creating the macro-roughness. Additional coatings, for example of apatite, are not needed and are also preferably not present.

The surface modified by the salt melt proves particularly suitable when the implant is provided at least on the surface with a layer of ceramic, or when, as is preferred, the implant is made almost entirely of ceramic.

The ceramic used can be of various types that are known from the prior art. For example, a ceramic can be used which contains titanium oxide or zirconium oxide, with optional addition of yttrium oxide and/or hafnium oxide. See, for example, U.S. Pat. No. 6,165,925, whose disclosure in terms of the composition and production of such ceramics based on zirconium oxide is intended to be incorporated by express reference into the disclosure of the present description.

It is alternatively possible to use ceramics which contain aluminum oxide, with optional addition of silicon dioxide, iron(III) oxide and/or sodium oxide. It is likewise possible to use a ceramic which contains silicon nitride, with optional addition of silicon dioxide, iron(III) oxide and/or sodium oxide. Ceramics based on mixtures or multi-layer systems based on said materials are also possible.

According to a preferred embodiment, the implant is a dental implant whose surface exposed to the bone and/or soft tissue in the implanted state is modified at least in some regions in a salt melt.

The surface modified by the salt melt can be superposed with a macro-roughness, as has been described above, that is to say with a macro-roughness having pore sizes of more than 10 µm, preferably of more than 20 µm. This can involve the surface being modified by sandblasting.

The present invention further relates to a method for the production of an implant as described above. The method is characterized in that a ceramic implant (or also a metallic implant) is surface-modified in a salt melt, at least in the regions exposed to bone and/or soft tissue, if appropriate after a previous surface modification involving removal of material to create a macro-roughness. A salt melt bath is typically used for this purpose.

According to a first preferred embodiment of the method, the salt melt is a salt melt composed of alkali and/or alkaline earth nitrates, alkali and/or alkaline earth hydroxides or alkali and/or alkaline earth halogens, or a mixture of these salts.

It is generally preferable if the salt melt is a salt melt with at least one hydroxide, in particular with at least one alkali and/or alkaline earth hydroxide. The salt melt is preferably a (eutectic) salt melt exclusively composed of one or more hydroxides, in particular of one or more alkali and/or alkaline earth hydroxides. It is precisely the use of at least one alkali and/or alkaline earth hydroxide, preferably a mixture of such hydroxides, that leads unexpectedly to an optimal formation of the desired micro-roughness, as has been described above.

The mixtures can be binary, ternary, or even higher. A salt melt is preferably used which is composed essentially of alkali hydroxides, for example of potassium hydroxide and/or sodium hydroxide and/or lithium hydroxide. Small quantities, typically in the region of less than 5% or even less than 2%, of other salts (not only but preferably of the above-mentioned) or other additives may additionally be present, either to adjust the etching action or to adjust the melt temperature.

Salt melts that prove particularly suitable are, for example, binary salt melts, preferably of potassium hydroxide and sodium hydroxide, these two components being present in a ratio of 2:1 to 0.5:1, preferably in the range of 1.5:1-0.75:1. It has proven very particularly suitable if the ratio is chosen in the range of 1:1 or 7:5. In the case of such binary salt melts, particularly composed of said components, the work is preferably carried out at a temperature in the range of 100-600° C., particularly at a temperature in the range of 150-250° C.

Other salt melts that also prove particularly suitable are, for example, ternary salt melts composed of potassium hydroxide, sodium hydroxide and lithium hydroxide, these three components being present in a ratio in the range of 10-20:4-10:0.5-2, particularly in the range of 14:6:1. In the case of such ternary salt melts, work can preferably be carried out at a temperature of 100-400° C., particularly at a temperature in the range of 150-250° C.

It may generally be stated that a salt melt at a temperature in the range of 80° C.-1300° C. can typically be used, preferably in the range of 150° C.-600° C., particularly at a temperature in the range of 170-250° C.

According to another preferred embodiment of the method according to the invention, at least some regions of the surface are exposed to a salt melt, for example in the form of a bath, for a period of 10 minutes to 300 hours, preferably 10 to 100 hours, in particular 25 to 35 hours. A treatment period of at least one hour is preferably used, or more preferably of at least two hours, in order to ensure a sufficient removal of material from the implant by the salt melt and the formation of the micro-roughness according to the invention. Good results for the surface can be achieved when using, for example, binary mixtures or ternary mixtures, as are specified above, if the implant is exposed for 30 hours to a salt melt at a temperature of 100-210° C.

It proves advantageous if the implant surface is at least partially cleaned after the treatment with the salt melt. This can be done, for example, by ultrasound with deionized water, followed by washing and rinsing in deionized water.

Another preferred embodiment of the method is characterized in that the surface modification involving removal of material, particularly for creating the macro-roughness, is effected by blasting treatment, particularly by sandblasting. Such sandblasting preferably takes place using aluminum oxide particles with an average particle size of 0.05-0.25 mm or 0.25-0.5 mm. The work is preferably carried out with a pressure of between 1 and 10 bar, preferably of between 1 and 6 bar, particularly preferably of between 2 and 5 bar. The work is carried out especially at a pressure in the region of 4 bar.

The present invention further relates to an implant that is produced or can be produced by a method as described above.

The present invention further relates to a use of an implant, as described above, as a dental implant, in particular as a crown stump, as a threaded piece and/or pin.

Other preferred embodiments of the invention are described in the dependent claims.

BRIEF DESCRIPTION OF THE FIGURES

The invention will be explained in more detail below on the basis of illustrative embodiments and with reference to the figures, in which.

EMBODIMENTS OF THE INVENTION

Figure 1:
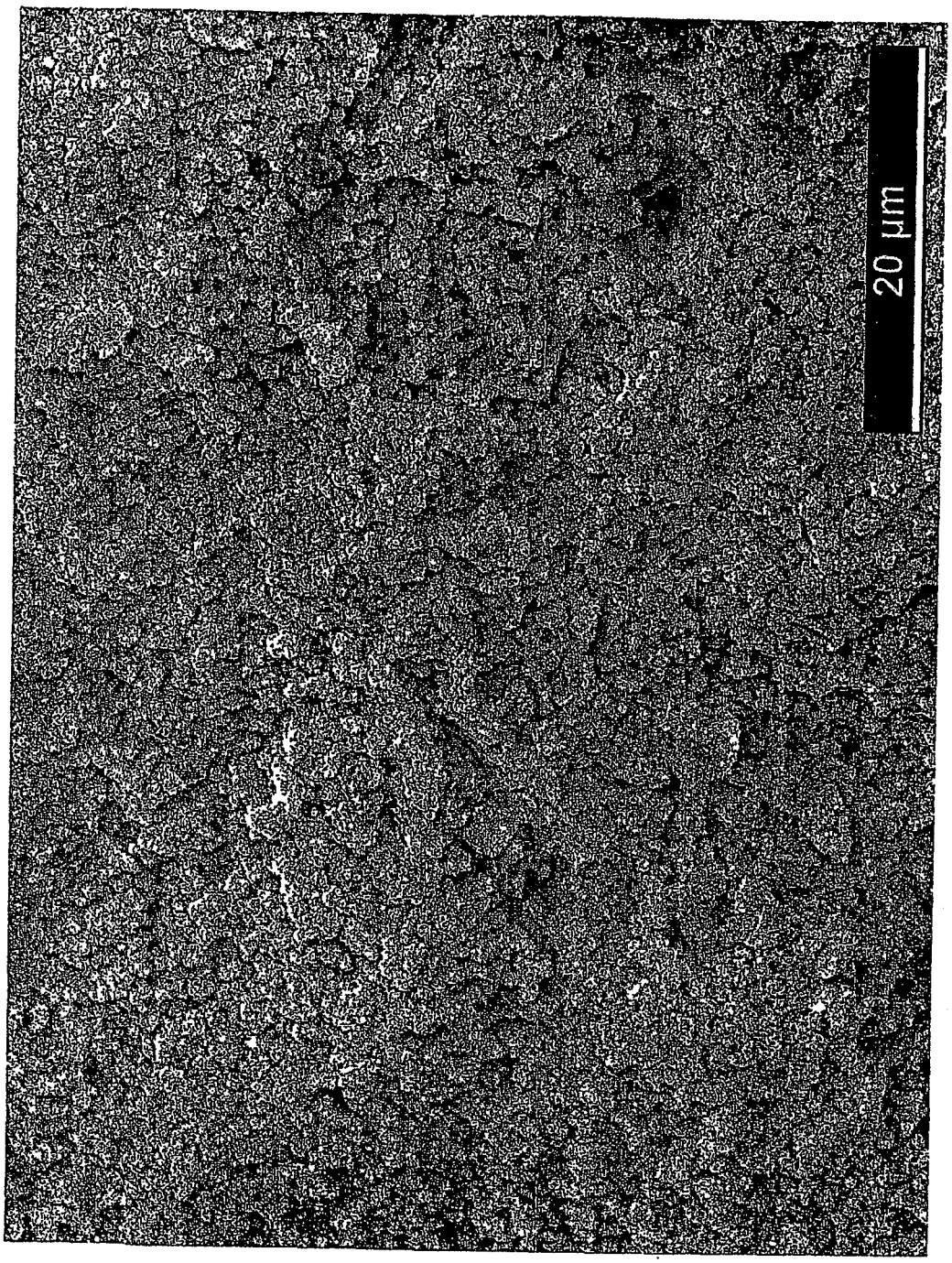
FIGS. 1 and 2 are SEM images at different resolutions, relating to Example 1 set out below.

The present invention describes the possibility of structuring the surface of implants which are made in particular from ceramic materials, but also from metallic materials. The purpose of the surface structuring is to obtain improved anchoring of the implants in hard tissue, an improved union between hard tissue and implant surface, an improved union between soft tissue and implant surface, and an improved interaction of the implant surface at the interface between implant surface and hard tissue and/or soft tissue.

The production of zirconium oxide, titanium oxide and aluminum oxide and/or of mixed ceramics for implants is known in principle in the prior art and will therefore not be discussed in any more detail. In this context, reference is made, for example, to the disclosure of the document already cited above, namely U.S. Pat. No. 6,165,925.

The invention preferably relates to implants which are anchored in the hard tissue and/or soft tissue and are used for the temporary or permanent replacement or support of parts of the locomotor apparatus that have been damaged as a result of accident, wear, deficiency or disease or have otherwise degenerated, including in particular the masticatory apparatus in the dental field, together with the associated esthetic aspects. Thus, for example, hip-joint and knee-joint prostheses, spinal column implants and dental implants have for many years been used in clinical practice.

According to the invention, the object of the improved osteointegration properties or osseointegration properties is achieved by suitable surface structuring or surface treatment of the (ceramic) surface of the implant, the treatment being able to be carried out not only in partial regions of the implant surface, but also across the entire implant surface. Surface structuring of this kind ensures that the otherwise biologically inert ceramics, preferably zirconium oxide, titanium oxide or aluminum oxide or mixtures thereof, can be integrated into the hard and/or soft tissue.

The structural and functional anchoring, for example of a tooth implant, in bone is generally achieved by creating a macro-roughness and/or an if appropriate additional micro-roughness. The macro-roughness on the surface can be obtained, for example, by a mechanical blasting process, and the micro-roughness can be subsequently obtained either in an additive process, using plasma technology, or in a subtractive process, using chemical etching. The degree to which the implant is firmly anchored in the bone can be determined by mechanical measurements. Numerous studies have shown that the sufficient anchoring of an implant in bone depends to a large extent on the nature of the surface of the implant, in particular the roughness of its surface.

The present invention describes a specific roughness, created in a novel manner, for obtaining an increased effective surface area for better osteointegration of implants made of ceramics, preferably titanium oxide, zirconium oxide or aluminum oxide or mixtures thereof. This biologically active surface according to the invention can be produced using a salt melt, if appropriate in combination for example with additional mechanical working and structuring, shotpeening, sandblasting and/or subsequent or preliminary chemical treatment, for example etching with acid or the like, or by a combination of such methods.

The surface according to the invention can be produced, for example, by providing the surface with the desired roughness or texture. In particular, the implant can be produced by the implant surface being shotpeened or sandblasted and/or by its being structured by plasma technology, and by the surface then being treated by a chemical process in a salt melt, until a suitable surface structuring has formed.

As has been mentioned, the implant is etched using a salt melt. Salt melts are, by definition, very versatile liquids composed of molten salts, but they have never before been used in the present context. Traditional salt melts have a temperature of 150° C. to 1300° C. In recent times, salts with low melt points have also been used in salt melts below 80° C. It has been surprisingly found, particularly for implants based on ceramics, that salt melts have an excellent etching action on the surface in order to permit integration into bone or soft tissue, whereas the traditionally used acid baths cannot adequately attack ceramics.

In the present field of use, the surface is preferably etched with a mixture of potassium hydroxide and sodium hydroxide, or the surface is etched with a mixture of potassium hydroxide, sodium hydroxide and lithium hydroxide. In addition to these binary or ternary mixtures, however, it is also possible to use salt melts based on a single salt. The surface is then treated by ultrasound with pure/deionized water and thereafter rinsed and washed with pure/deionized water.

A mixture of potassium hydroxide and sodium hydroxide in a ratio of 1:1 is preferably used, or the surface is alternatively etched with a mixture of potassium hydroxide, sodium hydroxide and lithium hydroxide in a ratio of approximately 14:6:1.

The method preferably entails the implant being sandblasted and then being etched in a salt melt with a mixture of potassium hydroxide and sodium hydroxide in a ratio of 1:1 or with a mixture of potassium hydroxide, sodium hydroxide and lithium hydroxide in a ratio of approximately 14:6:1 at a temperature of 150-400° C. The surface is then treated by ultrasound with pure/deionized water and rinsed and washed with pure/deionized water.

The implant can be sandblasted with aluminum oxide particles, for example, with an average particle size of 0.05-0.25 mm or 0.25-0.5 mm, and then etched in a salt melt with a mixture of potassium hydroxide and sodium hydroxide in a ratio of 1:1 or with a mixture of potassium hydroxide, sodium hydroxide and lithium hydroxide in a ratio of approximately 14:6:1 at a temperature of 150-400° C.

The blasting treatment can be carried out here, for example, with a pressure of between about 1 bar and 10 bar, preferably of between 1 and 6 bar, in particular of between 2 and 5 bar.

An etching treatment with a mixture of potassium hydroxide, sodium hydroxide and lithium hydroxide in a ratio of approximately 14:6:1 at a temperature of 150-400° C. is preferred in particular as a secondary treatment to the blasting treatment.

The etching in the salt melt can be carried out, for example, for a period of 10 minutes to 300 hours, preferably 10 to 100 hours, in particular about 25 to 35 hours.

The etching in the salt melt can be carried out at a temperature of 150° C. to 400° C., preferably at 180° C. to 220° C., in particular about 190° C. to 210° C.

An etching treatment in the salt melt is expediently followed by a cleaning step, for example by ultrasound with pure/deionized water and by washing in deionized water and subsequent rinsing in deionized water.

Implants that have been pretreated in this way make it possible to obtain a firm union with hard tissue and soft tissue.

EXPERIMENTAL PRODUCTION OF IMPLANTS

Example 1

Figure 2:
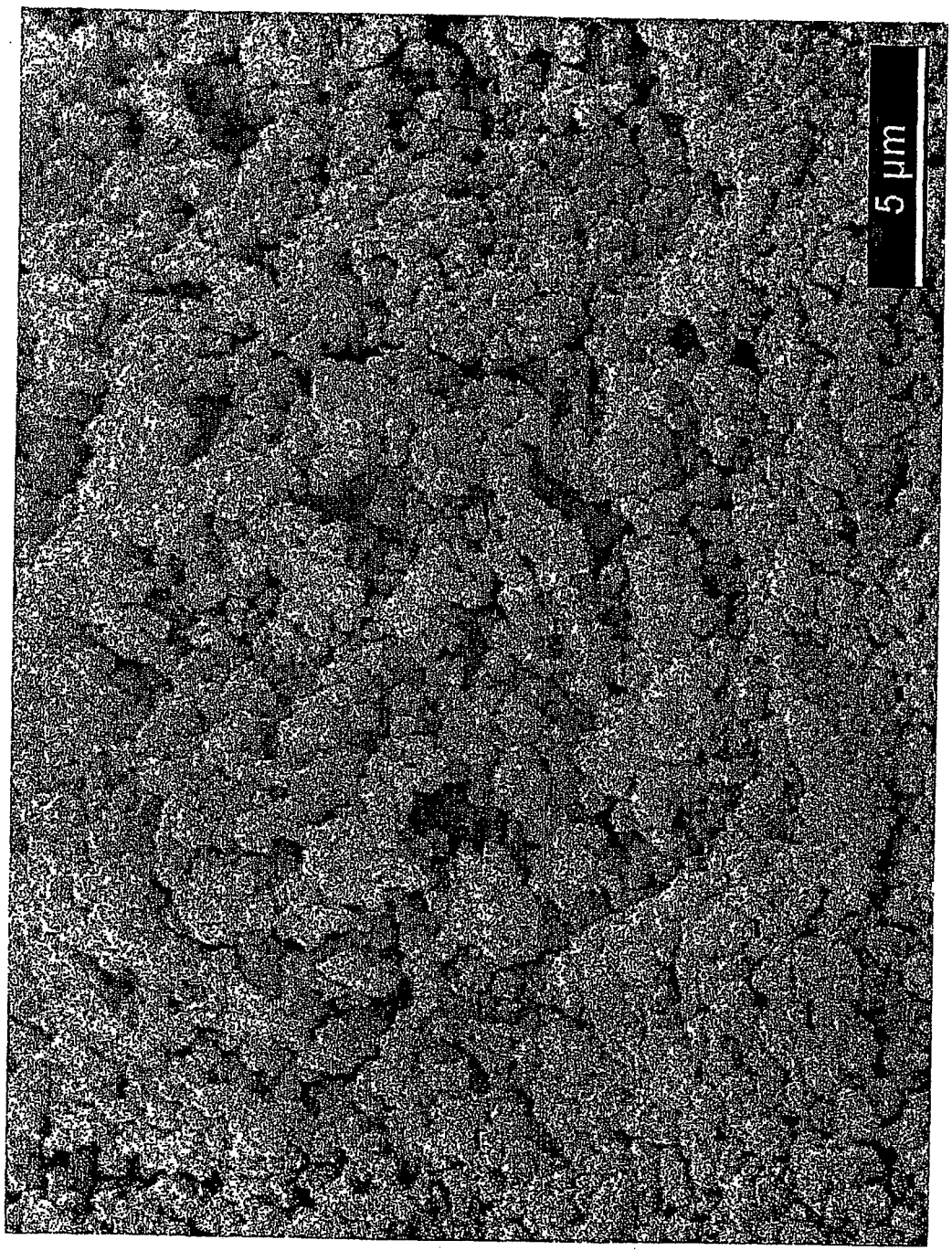

A common type of tooth implant in the form of a screw measuring 3.5 mm in diameter and 10 mm in length was produced from zirconium oxide. The basic shape was obtained from a cylindrical ceramic blank in a manner known per se in the mechanical working of ceramics, namely by grinding. The surface to be placed in the bone was then provided with a macro-roughness by being sandblasted with particles of $Al_2O_3$ of average particle size 0.1-0.15 mm at ca. 3 bar. The roughened surface (macro-roughness) was then treated with a mixture of potassium hydroxide and sodium hydroxide in a ratio of KOH:NaOH of 1:1 at a temperature of over 190° C. for approximately 30 hours. After the etching, the implant was treated by ultrasound with pure-deionized water and then washed and rinsed in deionized water. The resulting surface has a topography as shown in FIGS. 1 and 2 (SEM). The images show that a defined macro-roughness and also a defined micro-roughness are obtained, which is excellent for osseointegration.

Example 2

Figure 3:
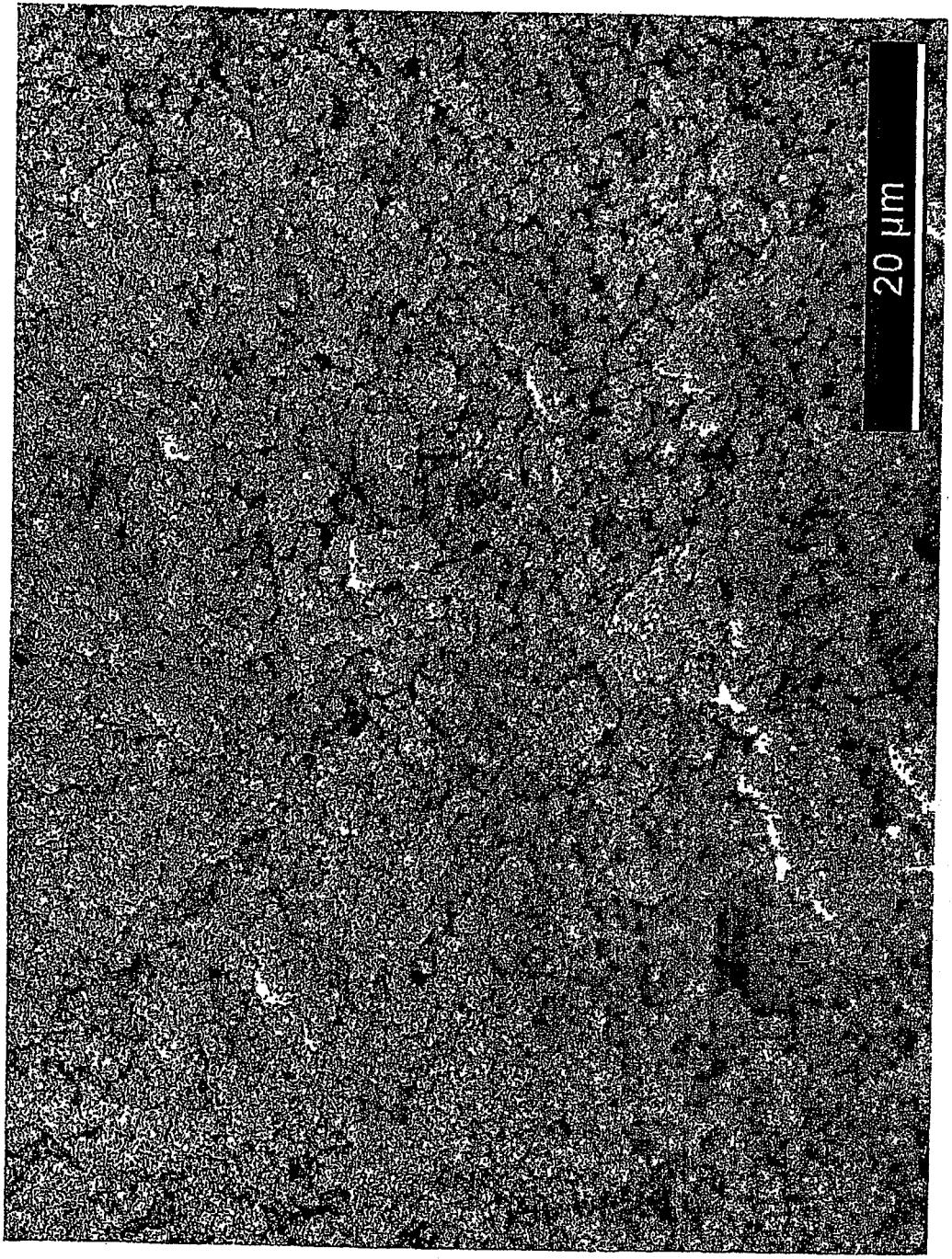
FIGS. 3 and 4 are SEM images at different resolutions, relating to Example 2 set out below.
Figure 4:
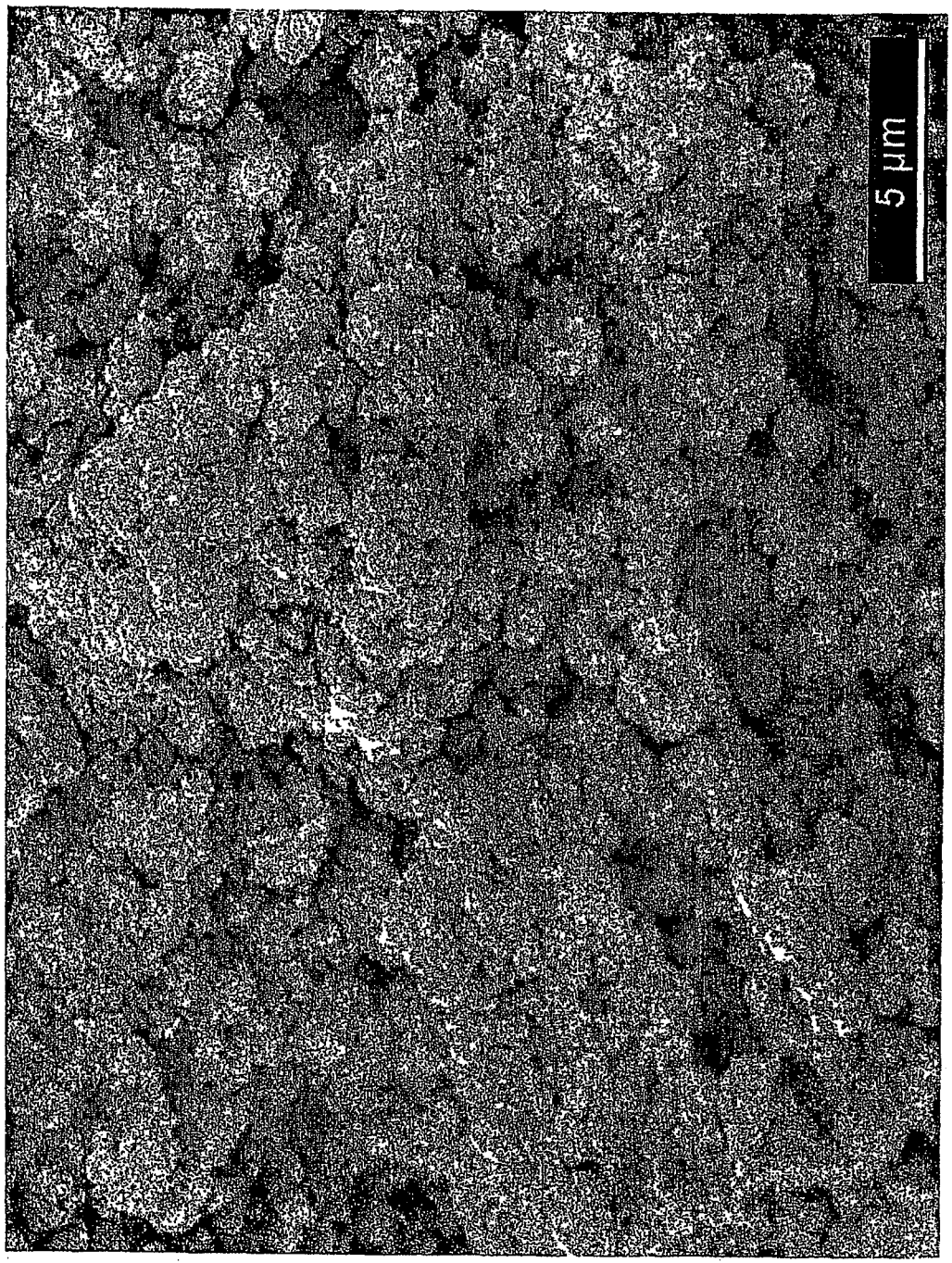

A common type of tooth implant in the form of a screw measuring 3.5 mm in diameter and 10 mm in length was produced from zirconium oxide. The basic shape was obtained from a cylindrical ceramic blank in a manner known per se in the mechanical working of ceramics, namely by grinding. The surface to be placed in the bone was then provided with a macro-roughness by being sandblasted with particles of $Al_2O_3$ with an average particle size of 0.1-0.15 mm. The roughened surface (macro-roughness) was then treated with a mixture of potassium hydroxide, sodium hydroxide and lithium hydroxide in a ratio of KOH:NaOH:

LiOH of 14:6:1 at a temperature of over 190*C for approximately 30 hours. After the etching, the implant was treated by ultrasound with pure-deionized water and then washed and rinsed in deionized water. The resulting surface has a topography as shown in FIGS. 3 and 4 (SEM). The images again show that a defined macro-roughness and also a defined micro-roughness are obtained, which is excellent for osseointegration.

Example 3

A common type of tooth implant in the form of a screw measuring 3.5 mm in diameter and 10 mm in length was produced from zirconium oxide, and its surface was treated in the manner described in Example 2. In a departure from Example 2, not only was the surface for placement in the bone provided with roughness, but also the surface to be placed in the soft tissue.

Example 4

A common type of ceramic implant in the form of an acetabulum of size 44 was produced from zirconium oxide. The basic shape was obtained using a green body, and this ceramic blank was sintered and worked in a manner known per se to give the finished product. The surface to be implanted in the bone was then provided with a macro-roughness by being sandblasted with particles with an average particle size 0.1-0.15 mm. The roughened surface (macro-roughness) was then treated with a mixture of potassium hydroxide and sodium hydroxide in a ratio of KOH:NaOH of 7:5 at a temperature of over 190° C. for approximately 30 hours. After the etching, the implant was treated by ultrasound with pure-deionized water and then washed and rinsed in deionized water.

Example 5

A common type of ceramic implant in the form of an acetabulum of size 44 was produced from zirconium oxide. The basic shape was obtained using a green body, and this ceramic blank was sintered and worked in a manner known per se to give the finished product. The surface to be placed in the bone was then provided with a macro-roughness by being sandblasted with particles with an average particle size 0.1-0.15 mm. The roughened surface (macro-roughness) was then treated with a mixture of potassium hydroxide, sodium hydroxide and lithium hydroxide in a ratio of KOH:NaOH:LiOH of 14:6:1 at a temperature of over 190° C. for approximately 30 hours. After the etching, the implant was treated by ultrasound with pure-deionized water and then washed and rinsed in deionized water.

In Vivo Tests:

All the implants produced in these examples were found to give good osseointegration or osteointegration. Moreover, there was also found to be good integration in soft tissue (e.g. gums).

Figure 5:
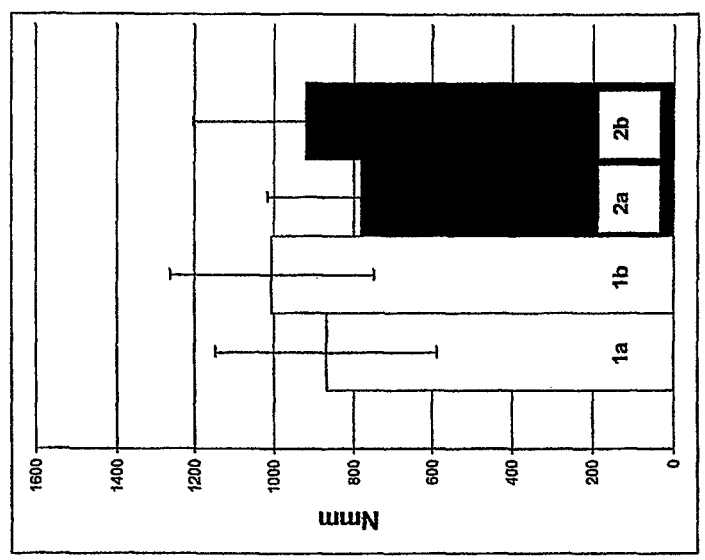
FIG. 5 shows the results of tests carried out with two implant types of different material and surface.

FIG. 5 shows corresponding results from tests carried out on two implant types made of different materials and with different surfaces. A ceramic implant with a diameter of 4.2 mm and a length of 8 mm, and with a surface produced according to the invention, essentially in accordance with Example 1 described above (measurement 1 in FIG. 5), was compared against a correspondingly dimensioned dental implant (titanium implant) with a surface anodized by plasma chemistry (measurement 2 in FIG. 5). The anodized surface produced by plasma chemistry corresponds to the surface of commercially available and widely used implants.

The implants were implanted into the iliac wings of sheep. After a healing time of 4 weeks (measurement a) and 8 weeks (measurement b), the torque needed to release the incorporated implants from the bone was determined.

As FIG. 5 shows, the novel implant provides better incorporation.

The invention claimed is:

1. A method for the production of a ceramic implant with a structured, porous surface having biocompatibility, for at least partial insertion into hard tissue and/or into soft tissue followed by osteointegration or osseointegration therewith, comprising:
    surface modifying the ceramic material on a ceramic surface area of said ceramic implant in a salt melt at least in the regions of said ceramic implant that are to be exposed to bone and/or soft tissue, if appropriate after a previous surface modification, involving removal of ceramic material,
    wherein the implant is structured on the ceramic surface area by etching in said salt melt, and
    wherein the etching in said salt melt changes the topography of the ceramic surface and forms a porous surface, and involves essentially only a removal of some ceramic material from the entire surface of said ceramic surface area while retaining other ceramic material on said entire surface of said ceramic surface area; and
    whereby a resulting final ceramic implant product comprises said porous ceramic surface with changed topography and having said biocompatibility without a coating of apatite.

2. The method as claimed in claim 1, wherein the salt melt is a salt melt composed of alkali and/or alkaline earth nitrates or hydroxides, or a mixture of these salts.

3. A method for the production of a ceramic implant with a structured, porous ceramic surface having biocompatibility, for at least partial insertion into hard tissue and/or into soft tissue followed by osteointegration or osseointegration therewith, comprising:
    surface modifying the ceramic at a ceramic surface area of said ceramic implant in a salt melt, at least in the regions of said ceramic implant that are to be exposed to bone and/or soft tissue, if appropriate after a previous surface modification, involving removal of some ceramic material from the entire surface of said ceramic surface area while retaining ceramic material on the entire surface of said ceramic surface area,
    wherein the salt melt is a salt melt with at least one hydroxide, and
    whereby a resulting final ceramic implant product comprises said ceramic surface having porosity and a changed topography and having said biocompatibility without a coating of apatite.

4. The method as claimed in claim 3, wherein the salt melt is a salt melt exclusively composed of one or more hydroxide.

5. The method as claimed in claim 3, wherein the salt melt is a salt melt composed of potassium hydroxide and/or sodium hydroxide and/or lithium hydroxide.

6. A method for the production of a ceramic implant with a structured, porous surface having biocompatibility, for at least partial insertion into hard tissue and/or into soft tissue followed by osteointegration or osseointegration therewith, comprising:
    surface modifying a ceramic surface area of the ceramic implant in a salt melt, at least in the regions of said ceramic implant that are to be exposed to bone and/or soft tissue, if appropriate after a previous surface modification, involving removal of material, wherein the salt melt comprises at least one hydroxide, and wherein the salt melt is a binary salt melt composed of potassium hydroxide and sodium hydroxide in a ratio of 2:1-0.5:1, and whereby a resulting final ceramic implant product comprises said ceramic surface with porosity and a changed topography and having said biocompatibility without a coating of apatite.

7. A method for the production of a ceramic implant with a structured, porous surface, for at least partial insertion into hard tissue and/or into soft tissue, comprising:

surface modifying a ceramic surface area of the ceramic implant in a salt melt, at least in the regions of said ceramic implant that are to be exposed to bone and/or soft tissue, if appropriate after a previous surface modification, involving removal of material, wherein the salt melt comprises at least one hydroxide, and wherein the salt melt is a ternary salt melt composed of potassium hydroxide, sodium hydroxide and lithium hydroxide in a ratio in the range of 10-20:4-10:0.5-2.

8. The method as claimed in claim 3, wherein a salt melt is used at a temperature in the range of 80° C.-1300° C.

9. The method as claimed in claim 3, wherein at least some regions of the surface are exposed to a salt melt for a period of 10 minutes to 300 hours.

10. The method as claimed in claim 3, wherein the implant surface is at least partially cleaned after the treatment with the salt melt.

11. The method as claimed in claim 3, wherein the surface modification involving removal of material is effected by blasting treatment.

12. The method as claimed in claim 3, wherein the salt melt is a salt melt with at least one alkali and/or alkaline earth hydroxide.

13. The method as claimed in claim 3, wherein the salt melt is a salt melt exclusively composed of one or more alkali and/or alkaline earth hydroxides.

14. A method for the production of a ceramic implant with a structured, porous surface having biocompatibility, for at least partial insertion into hard tissue and/or into soft tissue followed by osteointegration or osseointegration therewith, comprising:

surface modifying a ceramic surface area of the ceramic implant in a salt melt, at least in the regions of said ceramic implant that are to be exposed to bone and/or soft tissue, if appropriate after a previous surface modification involving removal of material, wherein the salt melt comprises at least one hydroxide, and wherein the salt melt is a binary salt melt composed of potassium hydroxide and sodium hydroxide in a ratio of in the range of 2:1-0.5:1, the work being done at a temperature in the range of 150-250° C., and whereby a resulting final ceramic implant product comprises said ceramic surface with porosity and a changed topography and having said biocompatibility without a coating of apatite.

15. A method for the production of a ceramic implant with a structured, porous surface, for at least partial insertion into hard tissue and/or into soft tissue, comprising:

surface modifying a ceramic surface area of the ceramic implant in a salt melt, at least in the regions of said ceramic implant that are to be exposed to bone and/or soft tissue, if appropriate after a previous surface modification involving removal of material, wherein the salt melt comprises at least one hydroxide, and wherein the salt melt is a ternary salt melt composed of potassium hydroxide, sodium hydroxide and lithium hydroxide in a ratio in the range of 14:6:1, the work being done at a temperature of 150-400° C.

16. The method as claimed in claim 3, wherein a salt melt is used at a temperature in the range of 150° C.-600° C.

17. The method as claimed in claim 3, wherein at least some regions of the surface are exposed to a salt melt for a period of 25 to 35 hours.

18. The method as claimed in claim 3, wherein the implant surface is at least partially cleaned after the treatment with the salt melt, treated by ultrasound with deionized water and then washed in deionized water and rinsed.

19. The method as claimed in claim 3, wherein the surface modification involving removal of material is effected by sandblasting, using aluminum oxide particles with an average particle size of 0.05-0.25 mm or 0.25-0.5 mm, with a pressure of between 2 and 5 bar.

20. The method as claimed in claim 3, wherein the implant is made of ceramic at least on the surface or is made entirely of ceramic.

21. The method as claimed in claim 3, wherein the implant contains zirconium oxide, with optional addition of yttrium oxide and hafnium oxide, and/or wherein it contains aluminum oxide, with optional addition of silicon dioxide, iron(III) oxide and/or sodium oxide, and/or wherein it contains titanium oxide, and/or in that it is formed from mixtures of said materials.

* * * * *